United States Patent
Baschnagel

(10) Patent No.: US 11,192,696 B2
(45) Date of Patent: Dec. 7, 2021

(54) THERMAL TREATMENT PACK

(71) Applicant: Robert Baschnagel, Garden City, NY (US)

(72) Inventor: Robert Baschnagel, Garden City, NY (US)

(73) Assignee: NYCE INNOVATIONS, LLC., Canton, MA (US)

( * ) Notice: Subject to any disclaimer, the term of this patent is extended or adjusted under 35 U.S.C. 154(b) by 356 days.

(21) Appl. No.: 16/034,388

(22) Filed: Jul. 13, 2018

(65) Prior Publication Data

US 2019/0322423 A1    Oct. 24, 2019

Related U.S. Application Data

(60) Provisional application No. 62/604,611, filed on Jul. 14, 2017.

(51) Int. Cl.
*B65D 33/30* (2006.01)
*A61F 7/02* (2006.01)
*A61F 7/00* (2006.01)

(52) U.S. Cl.
CPC ............... *B65D 33/30* (2013.01); *A61F 7/02* (2013.01); *A61F 2007/0001* (2013.01); *A61F 2007/023* (2013.01)

(58) Field of Classification Search
CPC .... B65D 33/30; A61F 7/02; A61F 2007/0001; A61F 2007/023; A61F 2007/0225; A61F 2007/0228
USPC .......................................................... 607/114
See application file for complete search history.

(56) References Cited

U.S. PATENT DOCUMENTS

| | | | | |
|---|---|---|---|---|
| 4,706,672 A | * | 11/1987 | Jones | A61F 7/02 165/46 |
| 4,908,248 A | * | 3/1990 | Nakashima | A61F 7/10 383/37 |
| 5,295,949 A | * | 3/1994 | Hathaway | A61F 5/055 482/10 |
| 5,395,399 A | | 3/1995 | Rosenwald | |
| 5,727,544 A | | 3/1998 | Miura | |
| 6,589,272 B1 | * | 7/2003 | Sheikh | A61F 7/02 607/108 |
| 7,060,086 B2 | | 6/2006 | Wilson et al. | |
| 8,603,151 B2 | | 12/2013 | Latham | |
| 2001/0051820 A1 | | 12/2001 | Rich | |
| 2002/0032462 A1 | * | 3/2002 | Houser | A61B 17/11 606/213 |

(Continued)

OTHER PUBLICATIONS

International Search Report together with the Written Opinion from related International Application No. PCT/US2019/040917 dated Nov. 15, 2019.

*Primary Examiner* — Linda C Dvorak
*Assistant Examiner* — Nils A Potter
(74) *Attorney, Agent, or Firm* — Scully, Scott, Murphy & Presser, P.C.

(57) ABSTRACT

A thermal pack including: a pouch containing a thermal source; and a bendable and deformable support one of attached to or disposed within the pouch, the support being configured such that the pouch is deformed into a shape matching a contour of a body part and the pouch is maintained in the shape while applied to the body part by the support. The support can include one or more deformable elongated members extending in at least one direction of the pouch.

16 Claims, 18 Drawing Sheets

(56) References Cited

U.S. PATENT DOCUMENTS

| | | | |
|---|---|---|---|
| 2004/0167456 A1 | 8/2004 | Kingsford et al. | |
| 2004/0244412 A1 | 12/2004 | Trinh et al. | |
| 2005/0261755 A1* | 11/2005 | Bacino | A61F 7/02 607/114 |
| 2006/0004427 A1 | 1/2006 | Wilson et al. | |
| 2006/0081000 A1 | 4/2006 | Trinh et al. | |
| 2007/0156213 A1* | 7/2007 | Friedensohn | A61F 7/03 607/114 |
| 2008/0140166 A1 | 6/2008 | Von Hoffman et al. | |
| 2008/0147153 A1* | 6/2008 | Quincy | A61F 7/106 607/114 |
| 2008/0312722 A1 | 12/2008 | Wang | |
| 2009/0099631 A1* | 4/2009 | Augustine | A61F 7/0097 607/104 |
| 2009/0205106 A1 | 8/2009 | Sohn | |
| 2011/0093050 A1 | 4/2011 | Damkoehler | |
| 2016/0022480 A1 | 1/2016 | Biser et al. | |
| 2017/0209329 A1 | 7/2017 | Ishibashi et al. | |
| 2018/0243127 A1 | 8/2018 | Chavarry et al. | |

\* cited by examiner

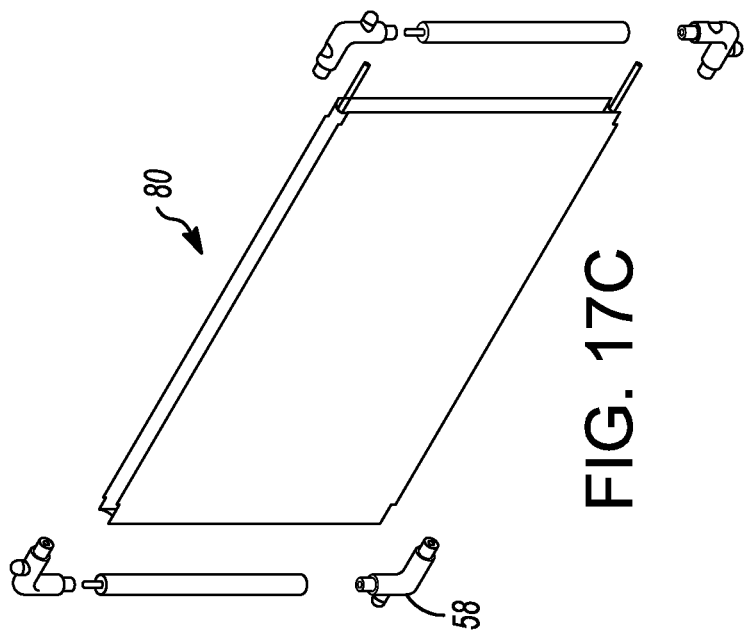
FIG. 17C
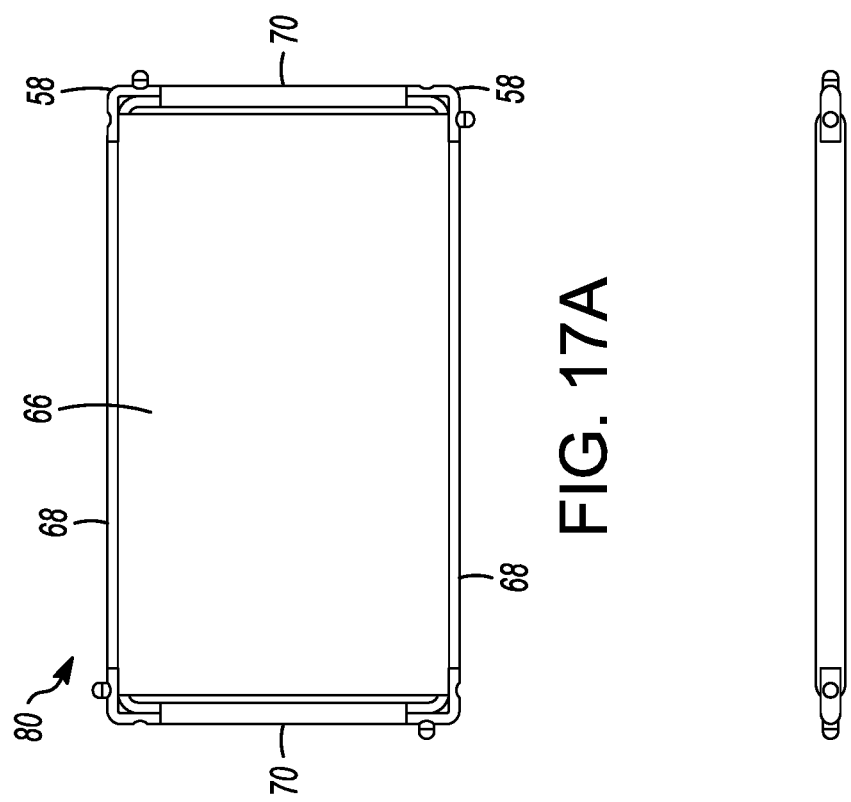
FIG. 17A
FIG. 17B

THERMAL TREATMENT PACK

CROSS REFERENCES TO RELATED APPLICATIONS

The present application claims priority to Provisional application 62/604,611 filed on Jul. 14, 2017 by the present inventor and entitled "A Thermal Treatment Pack".

Reference to Federally sponsored research or development: NA

Reference to joint research agreements: NA

Reference to Sequence Listing: NA

BACKGROUND OF THE INVENTION

Field of the Invention

The present invention relates generally to treatment by applied temperature controlled materials, and, in particular, relates the treatment of pain or soreness, and, in greater particularity, relates to thermal treatment of pain or soreness by applied hot or cold packs.

Numerous types of ice packs and heat packs use straps for holding the packs to the body.

Further, many devices are shown in issued patents and patent applications publications such as the following: US Patent Application Pub. 2001/0051820 shows thermal treatment packs and the retainers for such. These are highly configurable with the use of cloth strips with fasteners. US Patent Application Pub. 2004/0167456 shows a medical wrap about an ankle using hook and loop. Ice or heat packs may be placed thereunder. US Patent Application Pub. 2004/0244412 shows a pouch for ice bags that is attached to clothing by safety pins. US Patent Application Pub. 2001/0051820 shows a pouch with adhesive tabs for attachment. US Patent Application Pub. 2006/0004427 shows a cylindrical tubular body of flexible material with a temperature retaining material therein that can be used on an arm or leg, but not a shoulder. US Patent Application Pub. 2006/0081000 shows a self-adhesive ice bag device pouch. US Patent Application Pub. 2008/0140166 shows a thermal pack with modules inside. One version is tubular. US Patent Application Pub. 2009/0205106 shows a tubular wrist band with elastic bands on the edges, but it does not provide for heating or cooling but for absorbing water on the wrist. US Patent Application Pub. 2011/0093050 shows a thermal wrap with a pouch for foot use. The wrap is held in place by Velcro straps. U.S. Pat. No. 5,395,399 shows a thermal wrap with a pouch for thermal material and is held in place by an elastic cloth. U.S. Pat. No. 7,060,086 shows a tubular thermal pack for use on hands and legs. U.S. Pat. No. 8,603,151 shows a cooling device for application to body parts having an external thermal source and is held in place by straps. All of these references are incorporated by reference.

Thus, there is a need for a more convenient device to threat pain or soreness.

SUMMARY OF THE INVENTION

The present invention provides a flexible device for providing a source of thermal energy for treating pain or soreness in an arm, leg or shoulder.

A thermal pack may be applied to the body on an arm or leg or shoulder. A pouch for holding a thermal pack or being the thermal pack itself is held between parallel deformable, bendable rods that remain in that position to which bent until removed or adjusted. The rods may be on all four sides. The pack is generally rectangularly shaped with rounded corners, but other shapes may be considered. One end may be open and sealed by Velcro® after the appropriate thermal source whether a cooling source or heating source is placed therein, but the pouch may also hold a hot/cold therapy solution. The pouch may be an ice pack. If the source is the pouch, it is sold as a unit. The pack may come in various sizes for an arm, leg or shoulder. Additional features may be added to the pouch such as handles to aid in applying the pack. In general, the pack is held against the body part, i.e., wrist, and then bent around the wrist forming a "loosely" fitting cuff. This would be also done on the shoulder since the bendable rods will remain bent. The invention is directed at a person normally at rest and not contemplated for a person actively moving.

In another embodiment of the present invention, a gel pack being either a cold pack or a heat pack, is fixedly attached to the flexible rods and may be used also to keep foods warm or cold, for example.

It is an object of the present invention to provide a pack using thermal energy to treat pain or soreness;

It is another object of the present invention to provide a pack being either hot or cold in this treatment;

It is a further object of the present invention to provide a flexible thermal pack that loosely grips the body part and remains there while the body remains inactive;

It is still a further object of the present invention to provide thermal pack whose shape is controlled by flexible and deformable rods;

It is still another object of the present invention to provide a thermal treatment pack that does not require the use of straps;

It is still another object of the present invention to provide hot/cold therapy packs for active people such as baby boomers or elderly who have a limited range of motion, or for people who are out of shape where the bendable rods may be tightened for greater compression.

It is still another object of the present invention to provide a thermal treatment pack that is self-contained that can be temperature adjusted by cooling or heating the whole pack.

These and other objects, features, and advantages of the present invention will become more readily apparent from the attached drawings and the detailed description of the preferred embodiments, which follow.

BRIEF DESCRIPTION OF THE DRAWINGS

FIG. 17A shows by top view the thermal treatment pack; FIG. 7B shows a side view of the pack of FIG. 17A; FIG. 17C shows the thermal source with edge brackets bonded to the flexible rods thereabout with corner connectors for the flexible rods.

Like reference numerals refer to like parts throughout the several views of the drawings.

DETAILED DESCRIPTION OF THE PREFERRED EMBODIMENTS

In general, a thermal treatment pack is applied to the body on an arm or leg or shoulder. A pouch for holding a thermal pack or being the thermal pack itself is held between parallel deformable, bendable rods that remain in that position to which bent. The rods may be on all four sides. The pack is generally rectangularly shaped with rounded corners, but other shapes may be considered. One end may be open and sealed by Velcro® after the appropriate thermal source whether a cooling source or heating source, but the pouch may also hold a hot/cold therapy solution. The pouch may be an ice pack. If the source is the pouch, it is sold as a unit. The pack may come in various sizes for an arm, leg or shoulder. Additional features may be added to the pouch such as handles to aid in applying the pack. In general, the pack is held against the body part, i.e., wrist, and then bent around the wrist forming a "loosely" fitting cuff. This would be also done on the shoulder since the bendable rods will remain bent. The invention is directed at a person normally at rest and not contemplated for a person actively moving. In another embodiment of the present invention, a gel pack being either a cold pack or a heat pack, is fixedly attached to the flexible rod and may be used also to keep foods warm or cold.

Figure 1:
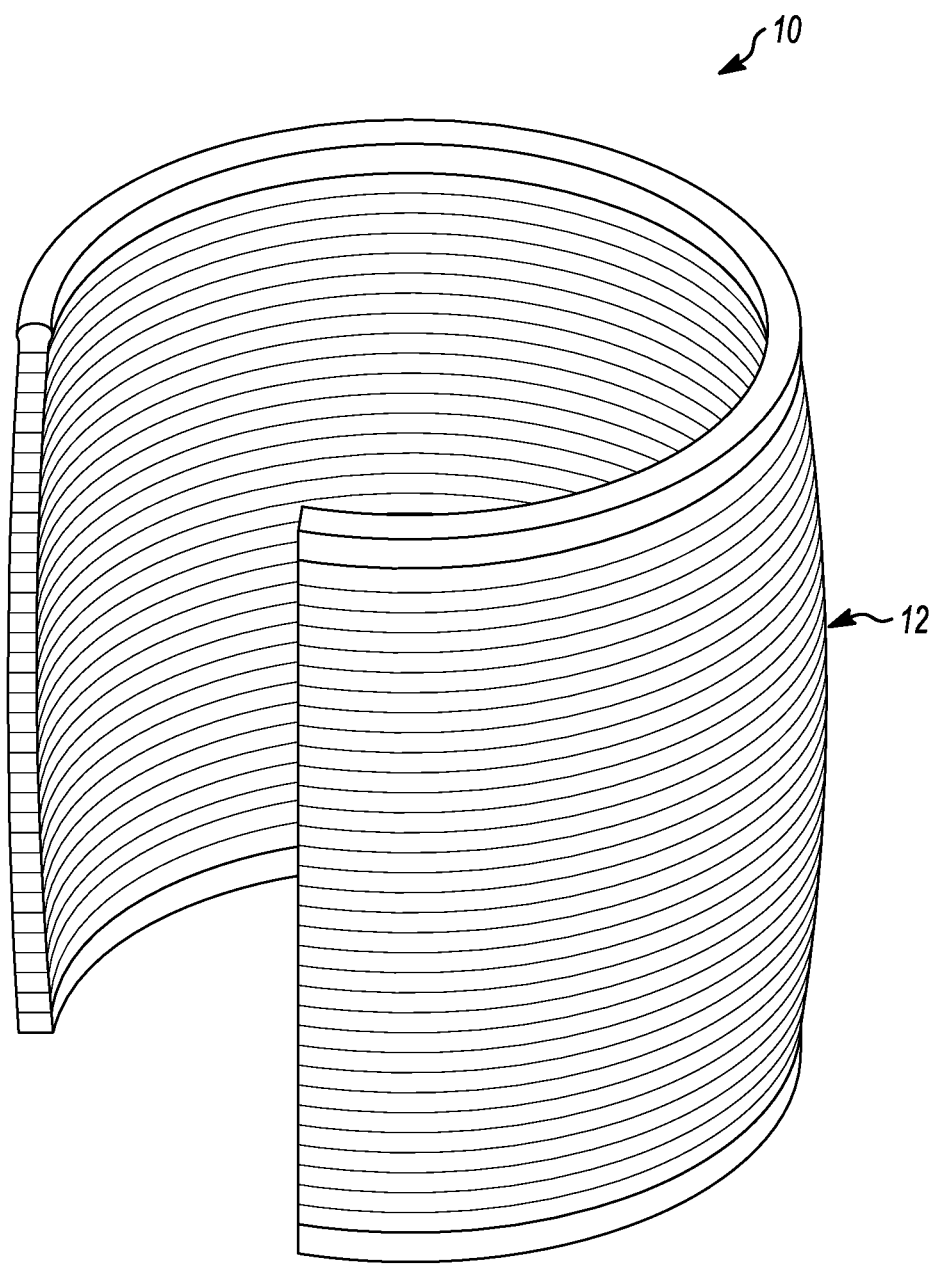
FIG. 1 is a perspective view of a thermal treatment pack formed into a cuff.
Figure 2:
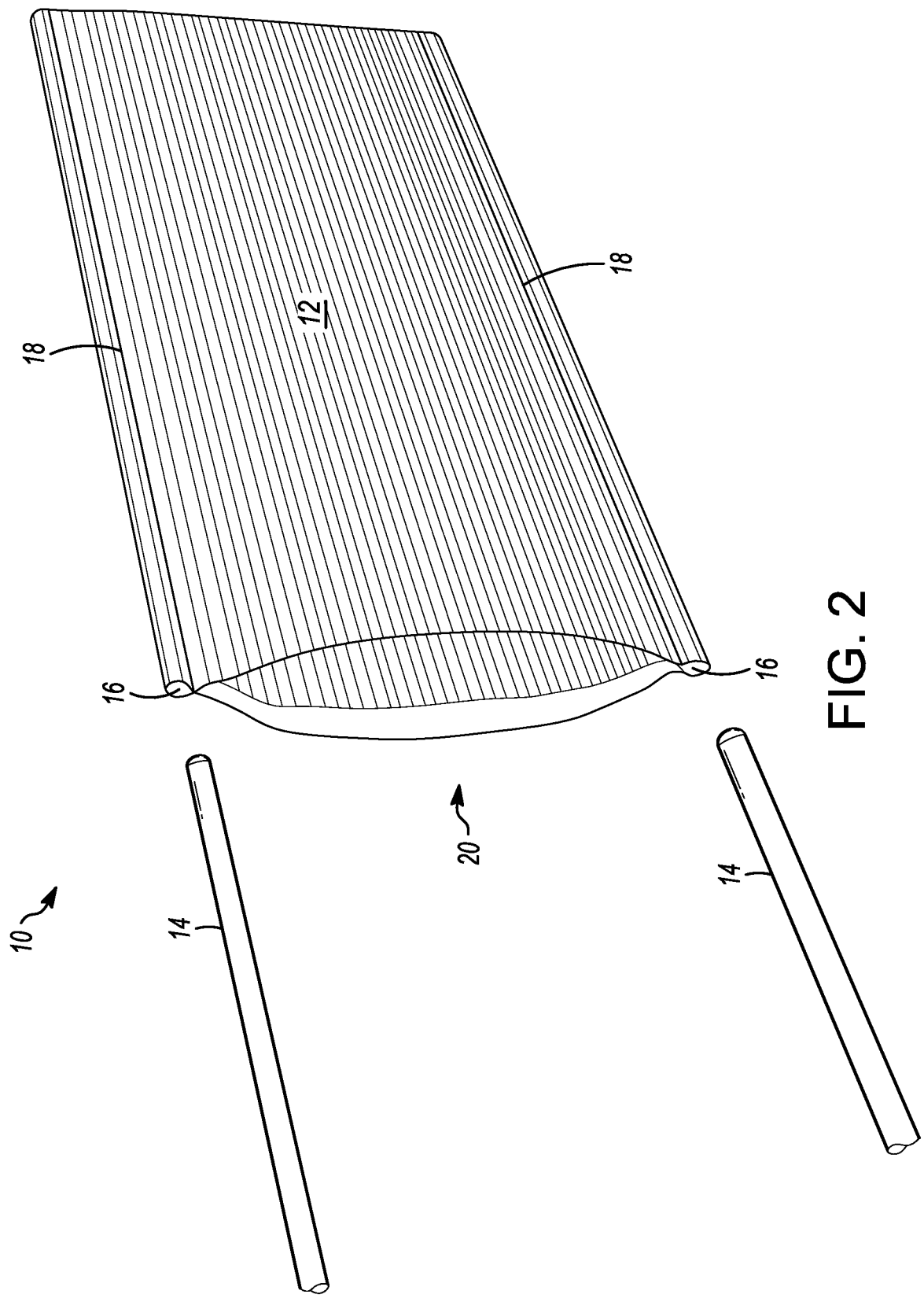
FIG. 2 is a perspective view showing the thermal treatment pack before the insertion of the flexible rods therein and before the insertion of a thermal source in a pouch of the present invention.

FIG. 1 shows a deformable thermal treatment pack 10 that can be applied to the body such as at a leg, arm and even a shoulder with a thermal source or pouch 12 therein. The pack 10 is bent like a cuff and will remain in that shape since deformable rods are placed thereabout. See FIGS. 7, 10 and 11. In FIG. 2, the pouch 12 is held between two parallel deformable, bendable rods 14 that are enclosed in cylindrical sleeves 16 as shown in FIGS. 2 to 6. These rods provide a support frame for the pouch. The bendable rods 14 form a support frame 17 about the pouch 12. The sleeves 16 are made by stitching away from the pouch edges 18 an appropriate distance inward. Other conventional means such as gluing or heat bonding can be used to form the sleeves depending on the materials. The pack 10 is generally rectangularly shaped but other shapes may be used. It may be about 2 to 4 inches on a short edge and 4 to 6 inches on a long edge for application to such locations as legs and arms. One end 20 may be open and sealed by Velcro™ after the appropriate thermal source 22, FIG. 5, whether a cooling source or heating source is inserted into the pouch 10.

Figure 7:
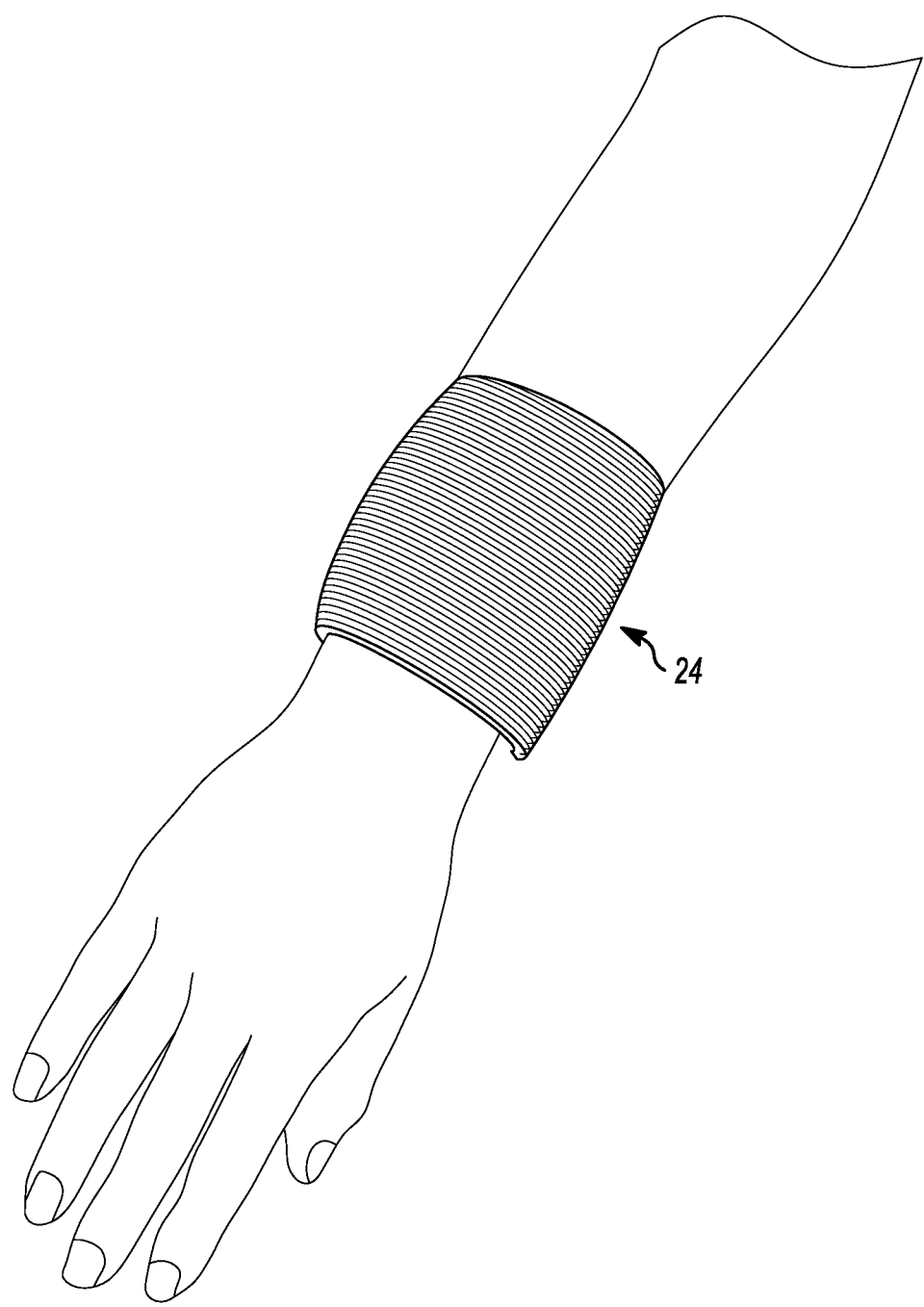
FIG. 7 shows the thermal treatment pack formed into a cuff and placed about a wrist.

In another embodiment, the appropriate thermal source whether an ice pack or hot/cold therapy solution may already be sealed in the pouch and sold as a unit. The walls of the pack 10 may be water impermeable then. The pack 10 may come in various sizes for an arm, leg or shoulder. FIG. 7, to be applied, the pack 10 is held against the body part, i.e., wrist 24, and then bent around the wrist 24 forming a cuff such as shown in FIG. 7. This would be also done on the shoulder and since the bendable rods will remain bent, the bent pack 10 will loosely grip the shoulder, but additional compression may be used or available. The pack 10 may tightly enclose a portion of the body part, and thus be sufficiently in contact with the skin to provide appropriate thermal treatment. The use of straps would not be required. Although the pack 10 is best used on inactive body parts, it can be also used in active movement The bendable rods may be on all four sides. The corner devices of the pack may be rounded. This product may be ideal for baby boomers, athletes, elderly with limited motion, and out-of-shape customers.

Figure 8:
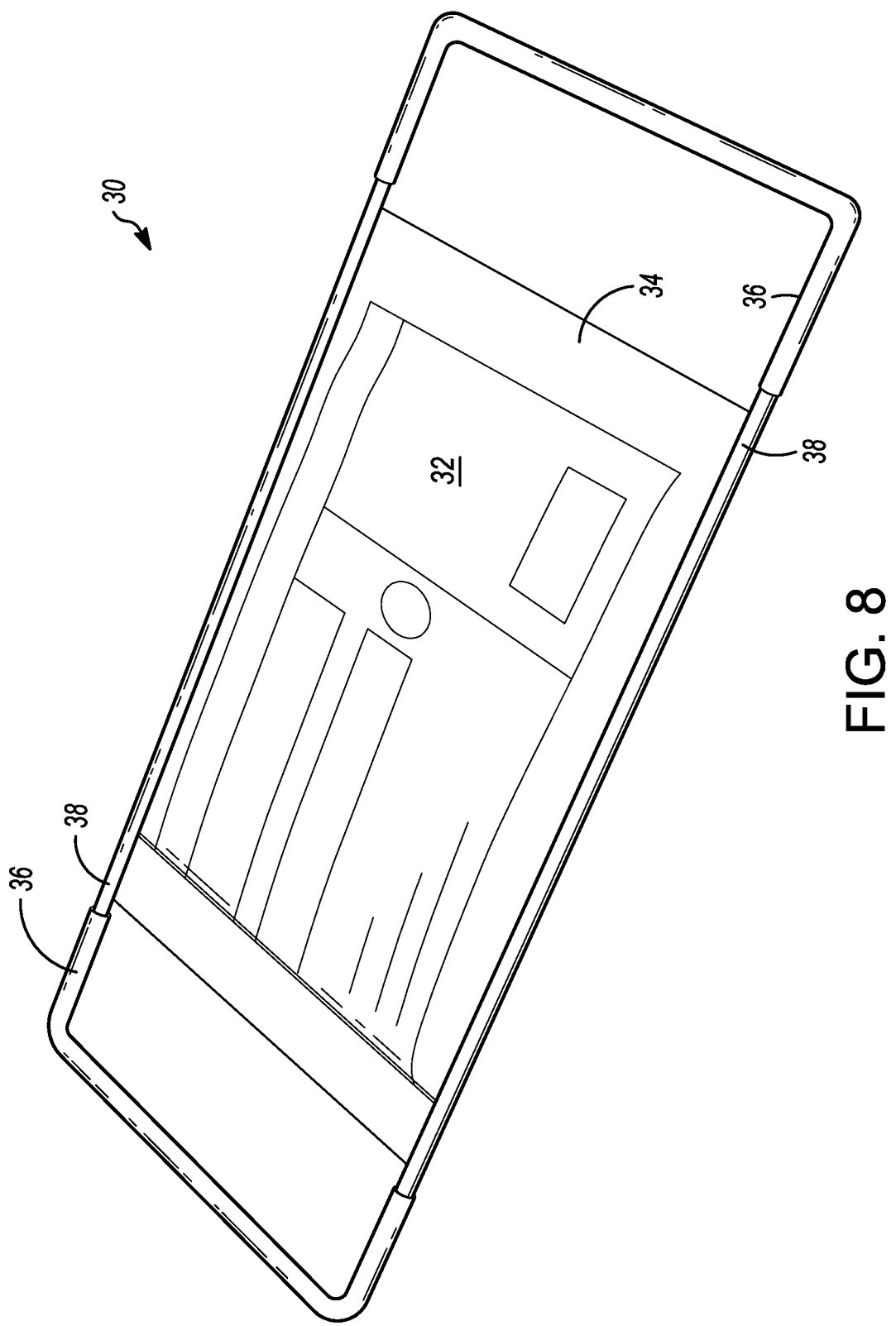
FIG. 8 shows the thermal treatment source with the heat source integrated into the pouch and further having handles thereon attached to the flexible rods
Figure 10:
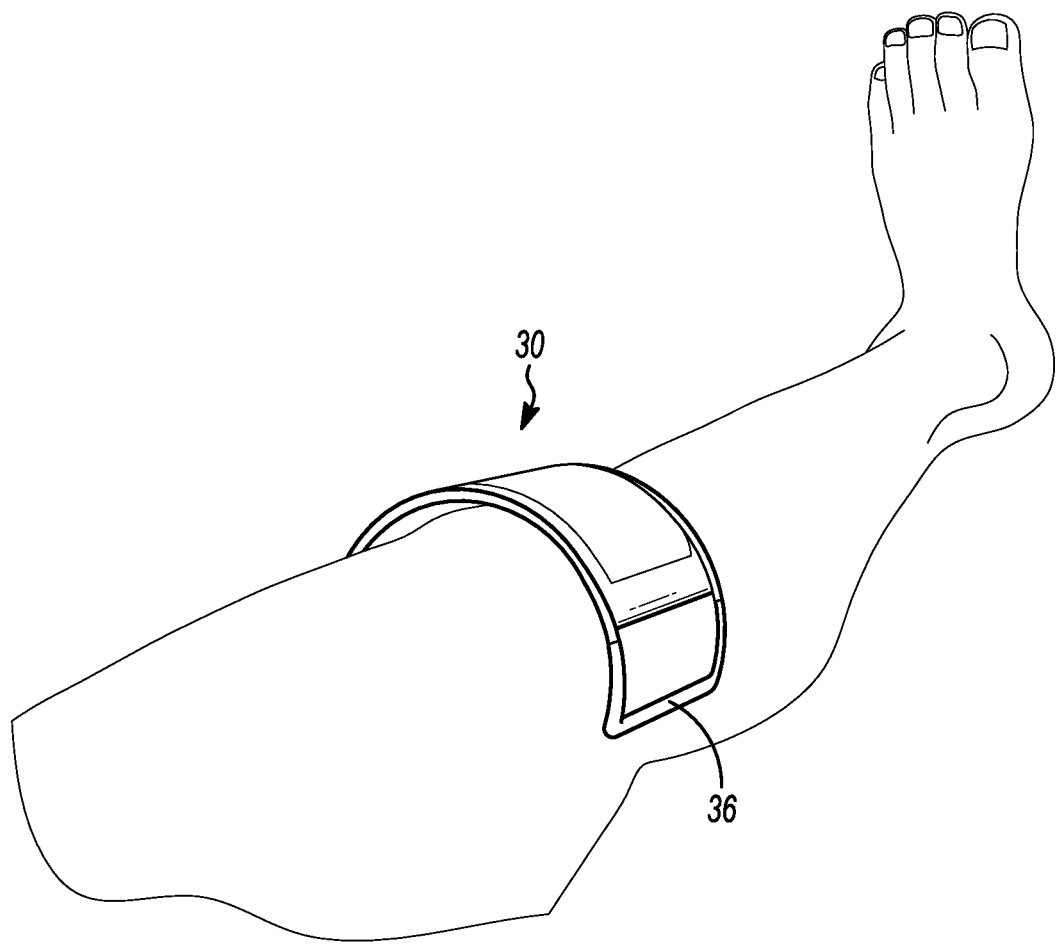
FIG. 10 shows the thermal treatment pack of FIG. 8 applied to a lower leg section with the handles gripping the leg.
Figure 11:
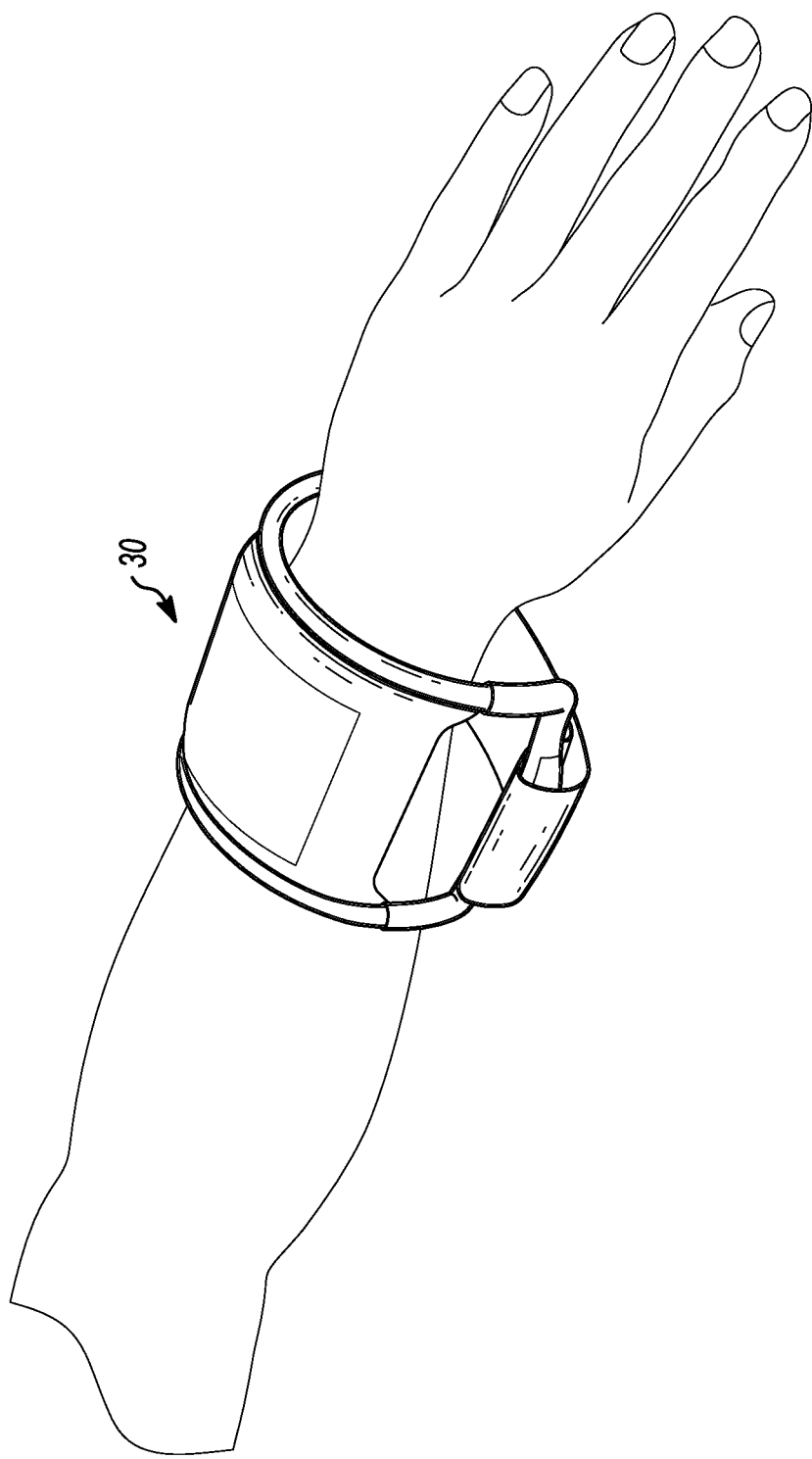
FIG. 11 shows the thermal treatment pack of FIG. 8 applied to a wrist by use of straps in the handles.

In another embodiment, FIG. 8 shows a thermal pack 30 with a thermal source 32 integrated into a pouch 34 and further having handles 36 thereon attached to the flexible, deformable and bendable rods 38 that provide a support frame. The handles 36 may be removed from the bendable rods 38, but can otherwise aid in the placement of the pack 30. The thermal source 32/pouch 30 is rectangular in shape and made of plastic-like material which would be waterproof. The thermal source 32 may be reusable by placing in a refrigerator or a microwave or a one-time use of heating or cooling material therein. The handles 36 provide a further reach about a body part that may have an irregular shape and may also be made of flexible, bendable rods like used in tie-wraps. The handles 36 shown are U-shaped. See FIGS. 14 to 17. FIG. 10 shows the thermal treatment pack 30 of FIG. 8 applied to a lower leg section, and FIG. 11 shows the thermal treatment pack 30 of FIG. 8 applied to a wrist.

Figure 9:
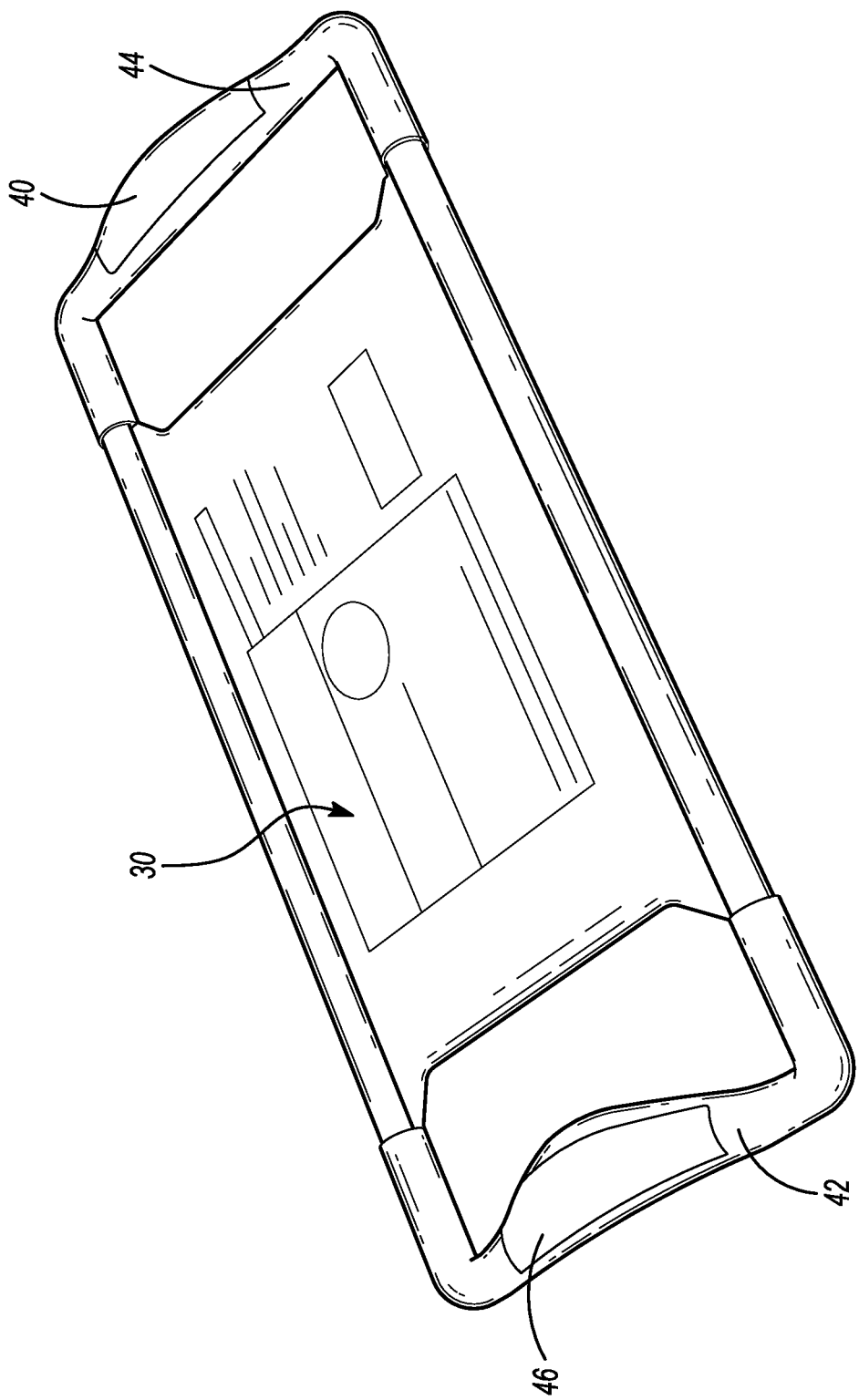
FIG. 9 shows alternative handles on the heat thermal treatment pack.
Figure 12:
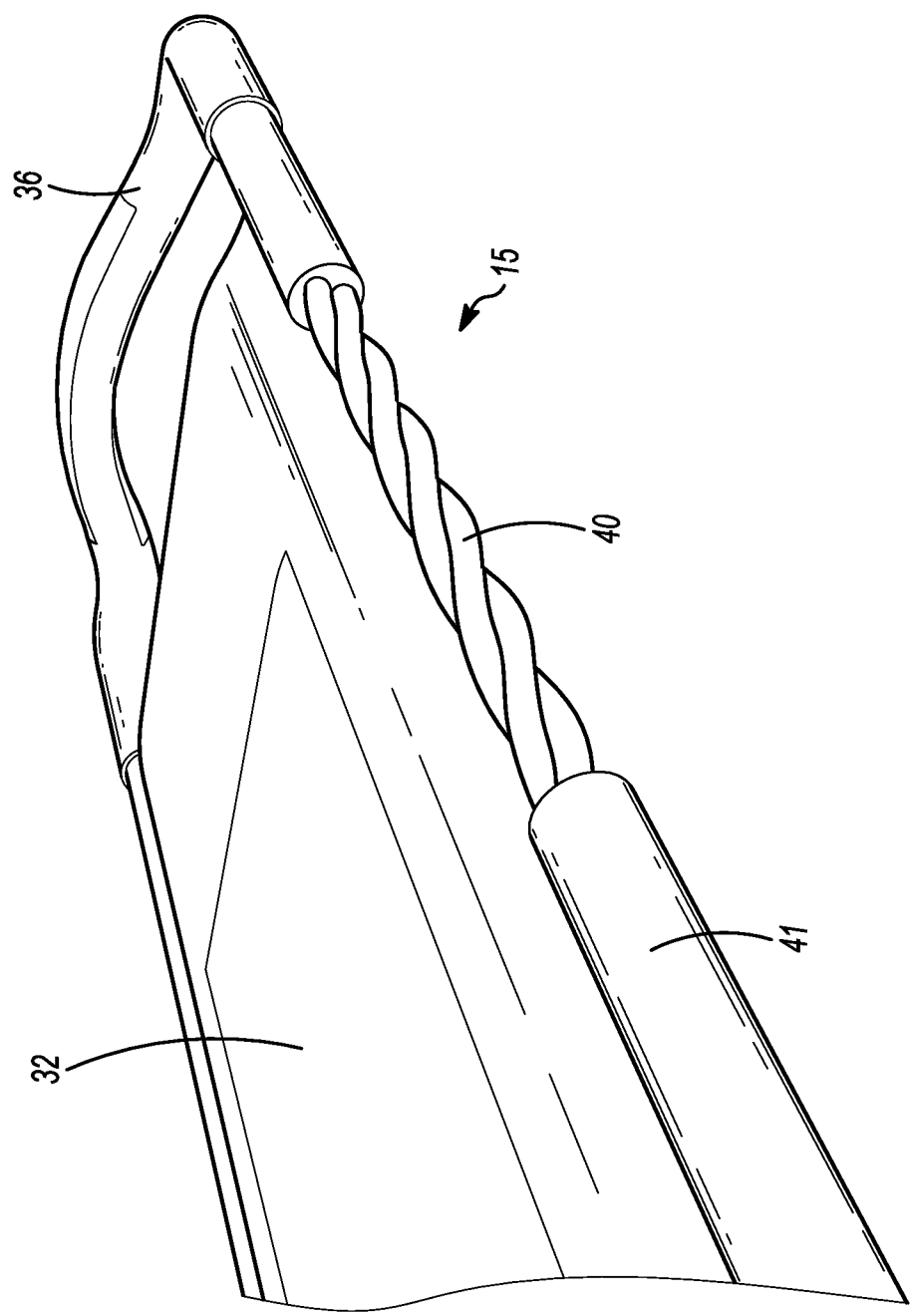
FIG. 12 shows partially a twisted wire as the frame with a foam or silicon cover supporting the thermal source of the present invention.
Figure 13:
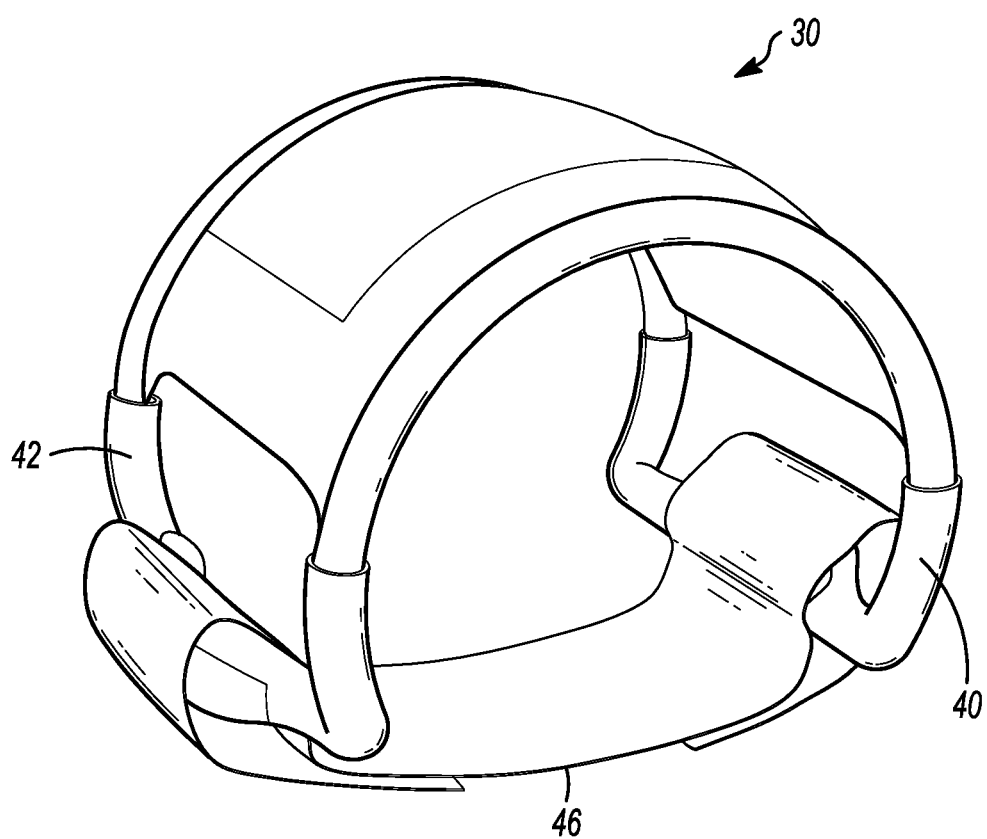
FIG. 13 shows a strap secured about the handles of the thermal treatment pack like that of FIG. 11 applied to a wrist.

FIG. 9 shows alternative handles 40 and 42 on the thermal treatment pack 30. The alternative handles 40 and 42 may have flattened sections 44 and 46, either being oriented perpendicular or parallel to the pouch. This provides for ease of handling and also for attachment of a strap 46 as shown in FIGS. 11, 12, and 13. With the use of a strap 46, the pack 30 can even be used on an active person.

Figure 3:
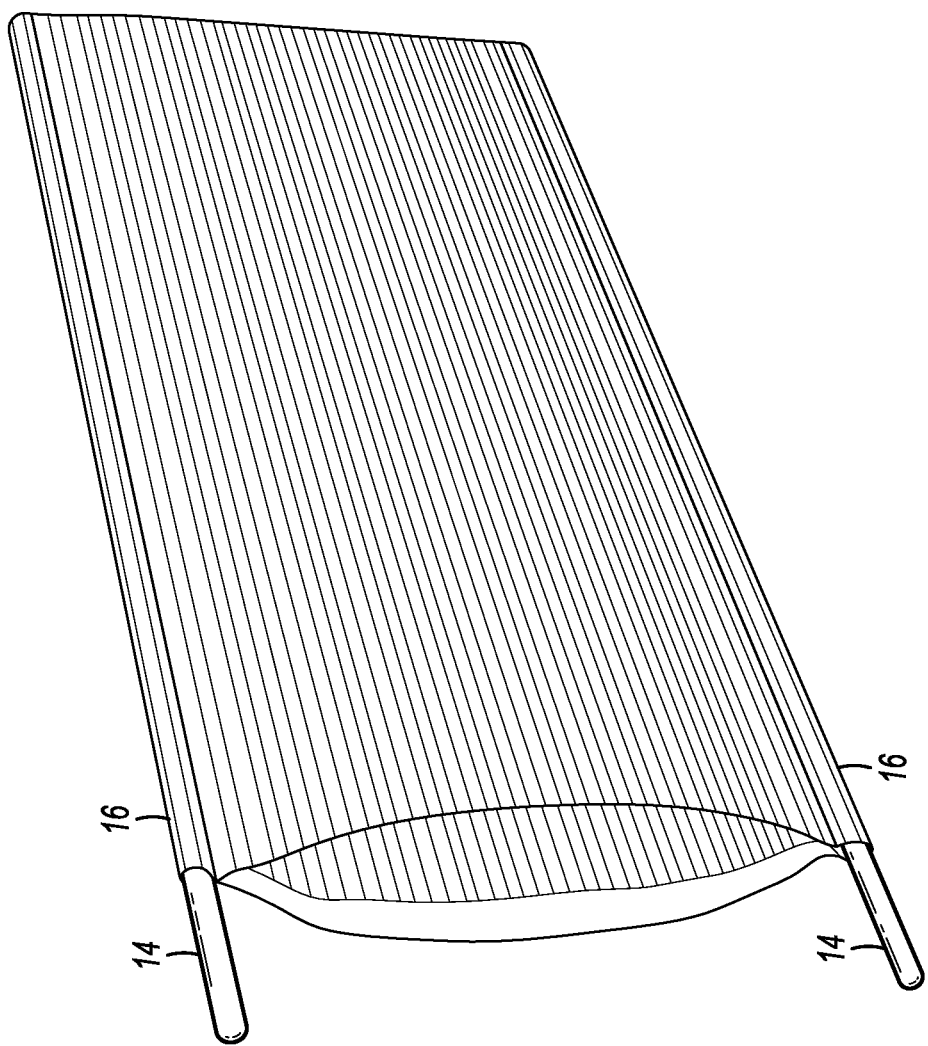
FIG. 3 is a perspective view of the thermal treatment pack as the flexible rods are being inserted of the present invention.
Figure 4:
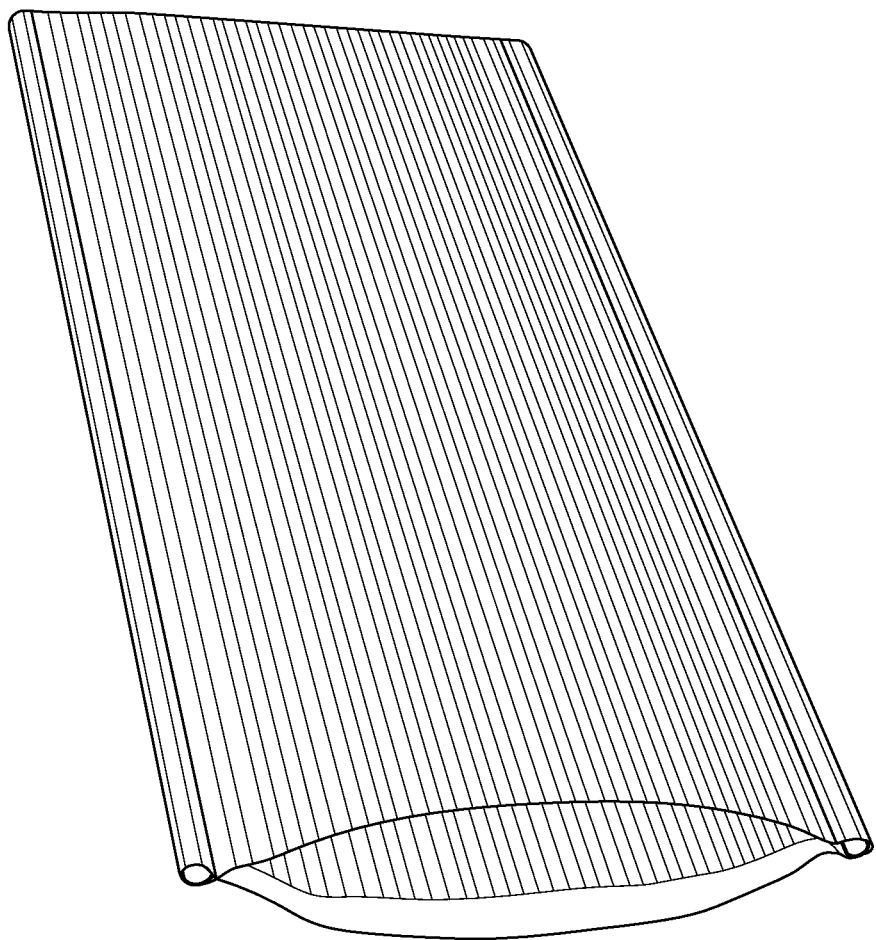
FIG. 4 shows the thermal treatment pack before the insertion of the heat source of the present invention.
Figure 5:
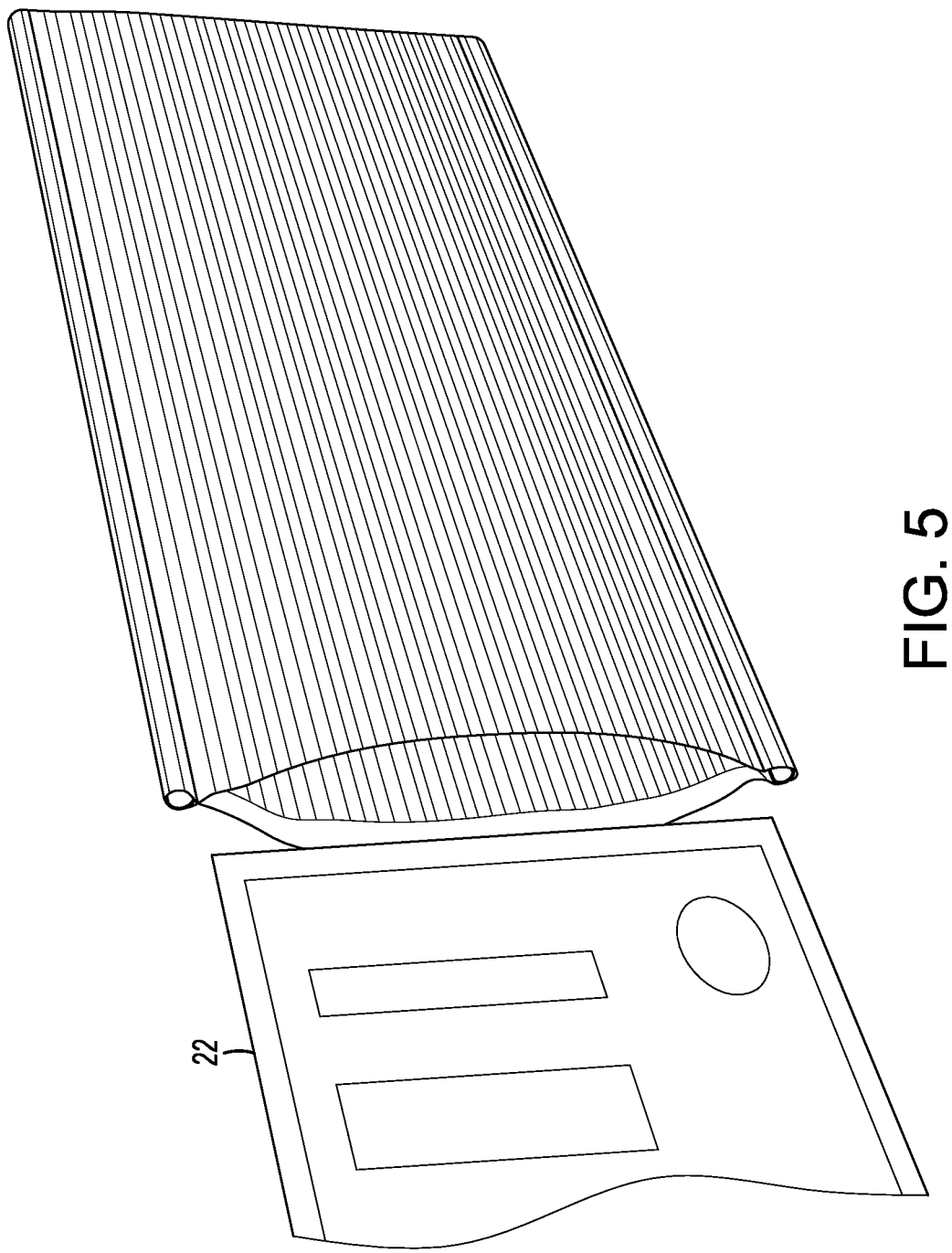
FIG. 5 shows the heat source being inserted into the pouch of the thermal treatment pack of the present invention.
Figure 6:
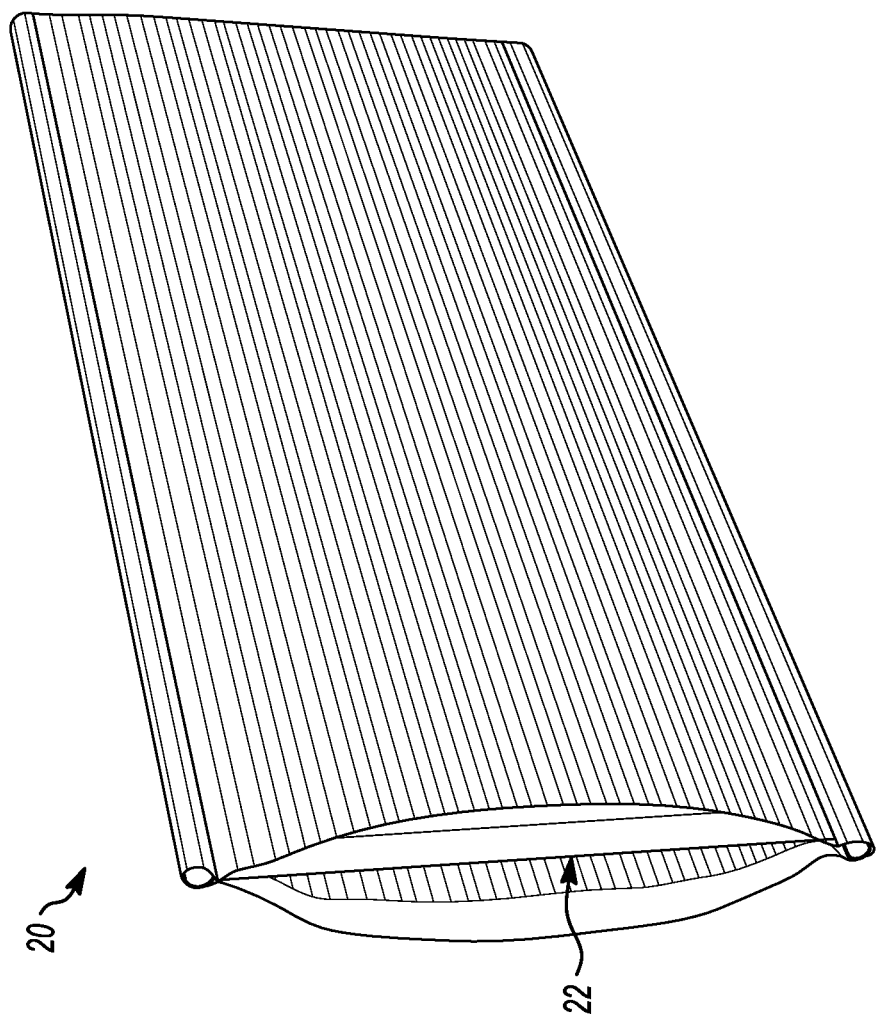
FIG. 6 shows the heat source within the pouch of FIG. 5.

Referring to FIGS. 2 and 3, the bendable or flexible or deformable rods 14 are like tie wraps. They are flexible, can be bent to a particular shape and will remain in that shape until bent further, and will resist bending to a certain degree. This rod may be made of a foam or silicon material thereabout with the twisted wires therein. See FIG. 12. These bendable rods 38 may be of tubular shape as shown. The bendable rods 41, in FIG. 12, may be twisted wires 40 inside of a tube 41.

Figure 14:
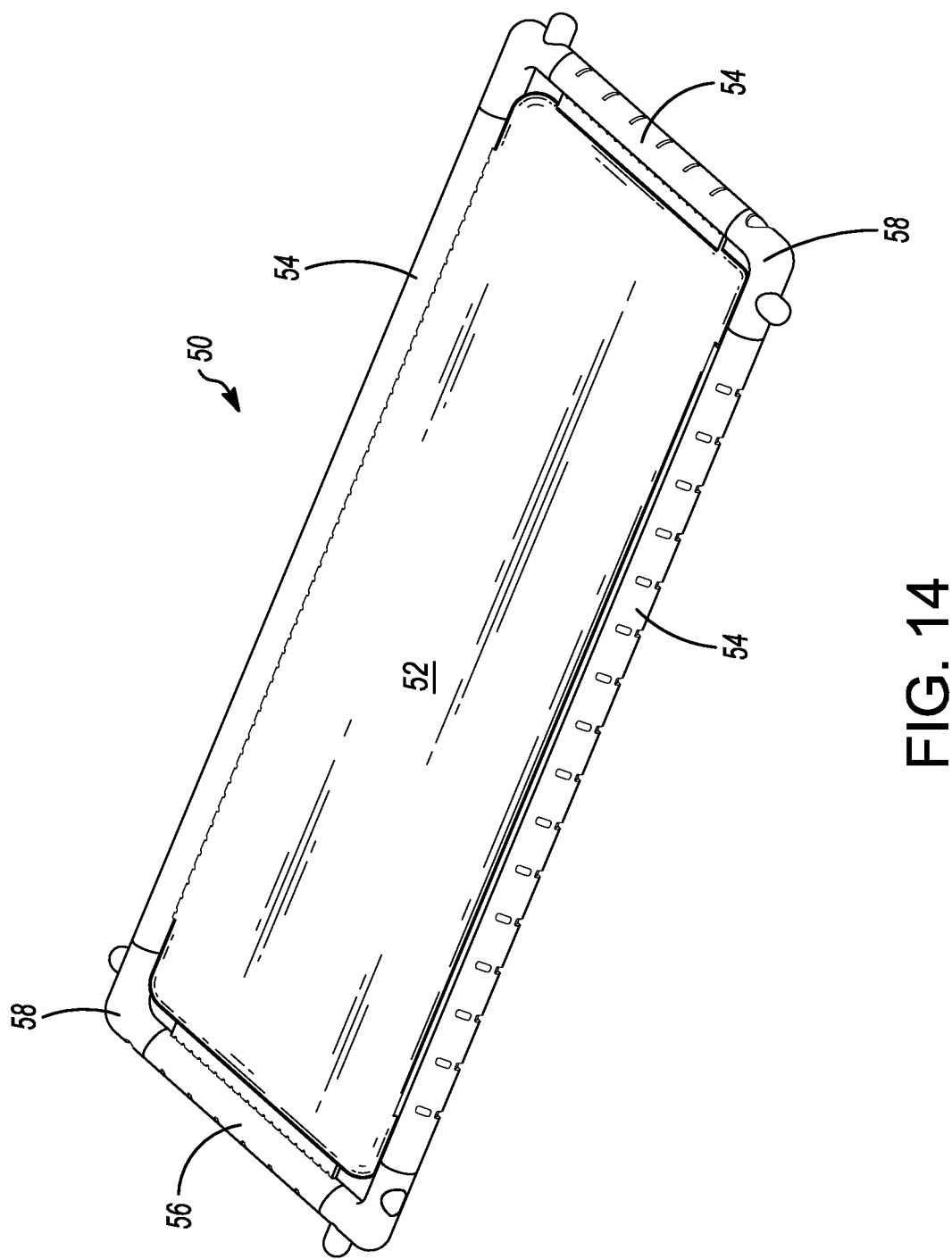
FIG. 14 shows a thermal treatment pack with the thermal source secured by bonding to the flexible rods thereabout.

Referring to FIGS. 14 to 17, in FIG. 14, a thermal treatment pack 50 is shown. A pouch 52 is designed to hold either cooling gel or heating gel or other material such as ice. The pouch 52 is plastic and is permanently and fixedly attached to two flexible side rods 54 being made of a foam or silicon material and having therein wires, not shown.

Further, two end rods 56 are also flexible if used. The side rods 54 and end rods 56 may be jointed together by corner support devices 58 that are typically rounded.

Figure 15:
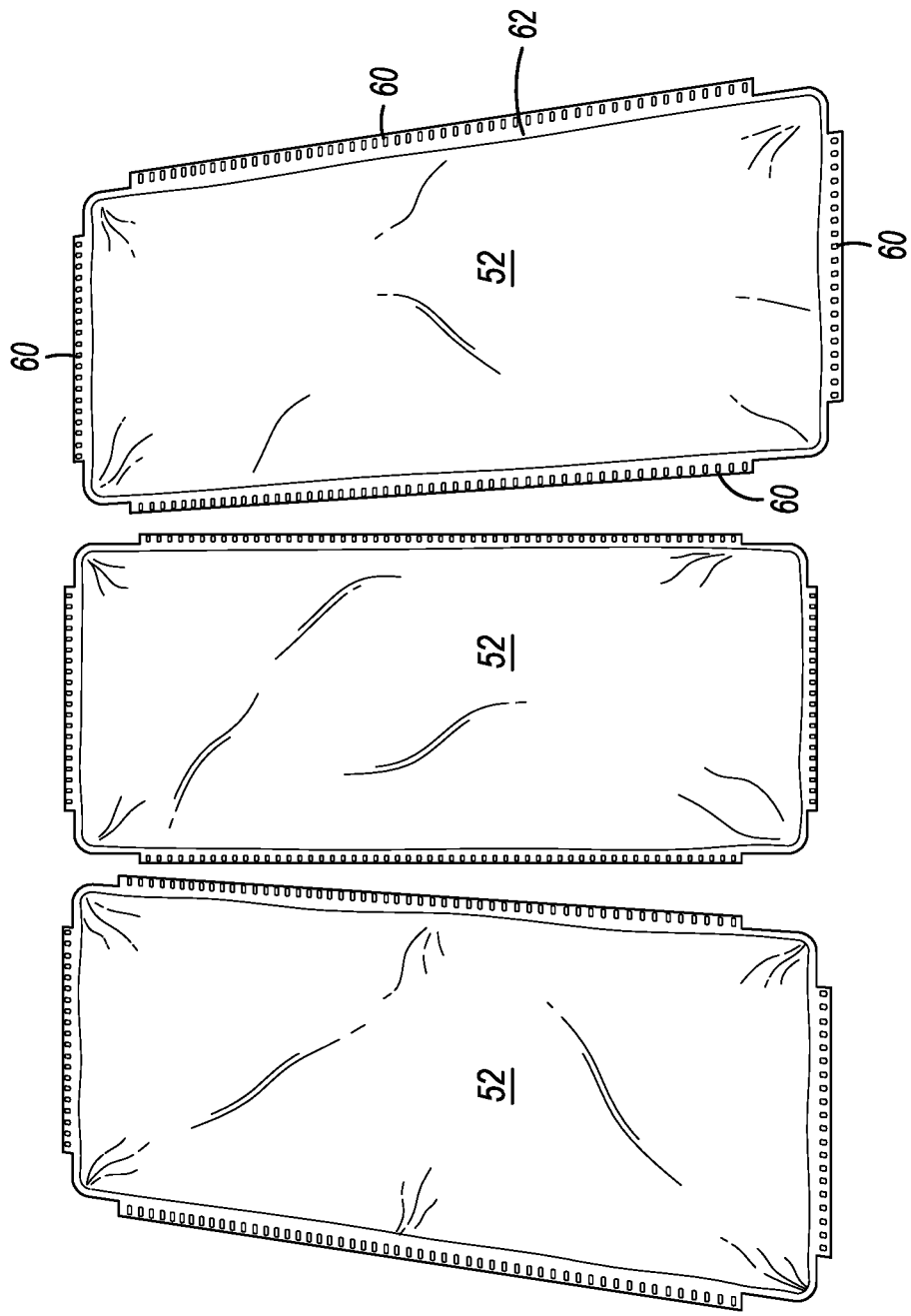
FIG. 15 shows the thermal source having edges for bonding to the flexible rods thereabout.

Referring to FIG. 15, the pouch 52 has extended edges 60 being made of similar material as the pouch 52. The pouch 52 may be about 3 to 4 inches wide and 6 inches long, but custom shapes are possible for such areas as the shoulder and neck. Other sizes may be used since it may be used on a leg having a larger diameter than a wrist. The extended edges 60 extend therefrom by about ¼ to ½ inch and has a plurality of slotted holes 62 running along the length. In the embodiment of FIG. 14, both the sides and the ends of the pouch have this extended edge 60 thereon.

Figure 16:
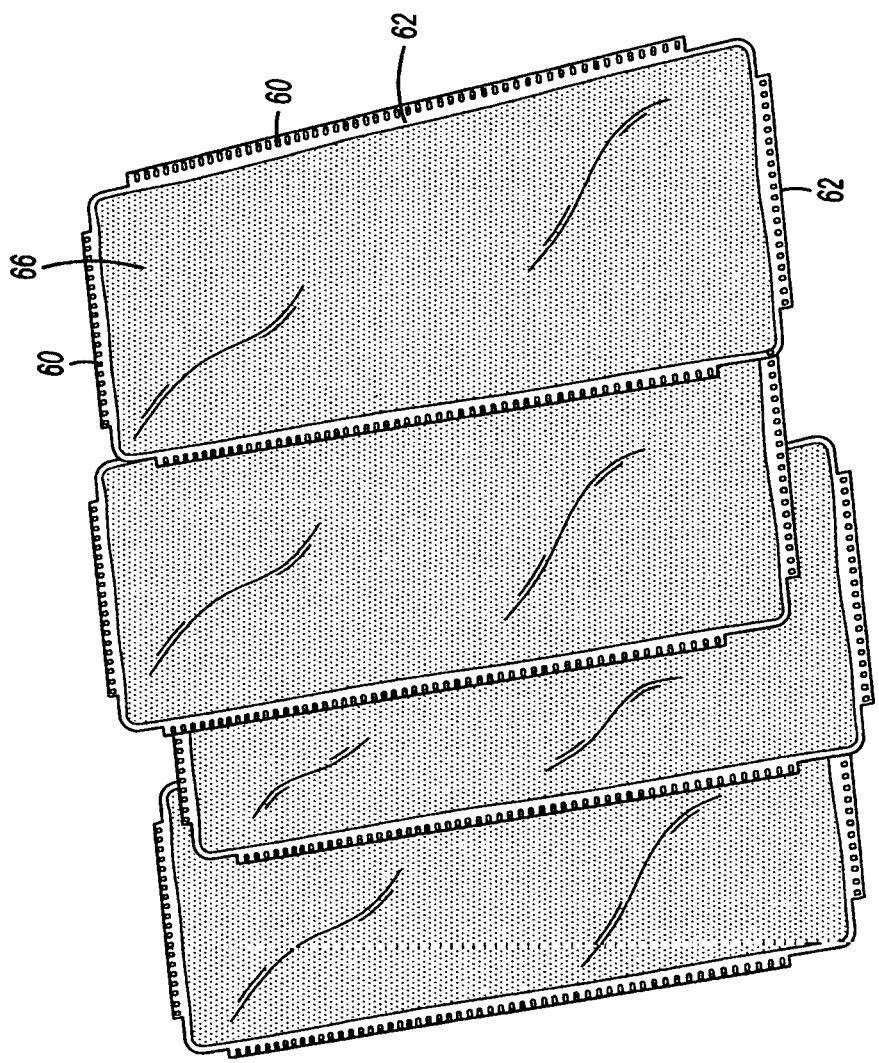
FIG. 16 shows thermal sources being gel packs having edge for bonding to the flexible rods thereabout.

These extended edges 60 used a vulcanization process to secure the edges 60 to the gel pack 52. The bendable rods 54/56 were enclosed in a foam or silicon or similar material and then secured to the edges 60 by ultrasonic welding. The pouches 52/60 have the extended edges on either the sides or the ends or both. The rods with corners are placed about the pouches 52/60. The pouch 52 shown in FIG. 14, being white, can hold material that maybe activated to provide heat. Referring to FIG. 16, pouch 66 shown may be blue in color and filled with cold gel that may be placed in a refrigerator for cooling. Similar edges 60 having a slotted pattern thereon allow for secure attachment to the rods by vulcanization.

To cover a large area, the pack 50 may be attached to similar packs 50 by use of snap fittings as shown in FIG. 14. Each side of the pack 50 has a male snap fitting 90 that may be a rounded post and a female snap fitting 92 that may be a hole into which the post closely fits. Further a dent on the post may further secure the post in the hole. The opposite snap fittings are attached to each corner device 58 and when constructed the other adjacent side has the snap fittings reversed so that one pack 50 may be pushed into an adjacent pack 50.

FIGS. 17A, 17B and 17C illustrate a pack 80 assembled and disassembled showing the various items thereon.

Figure 18A:
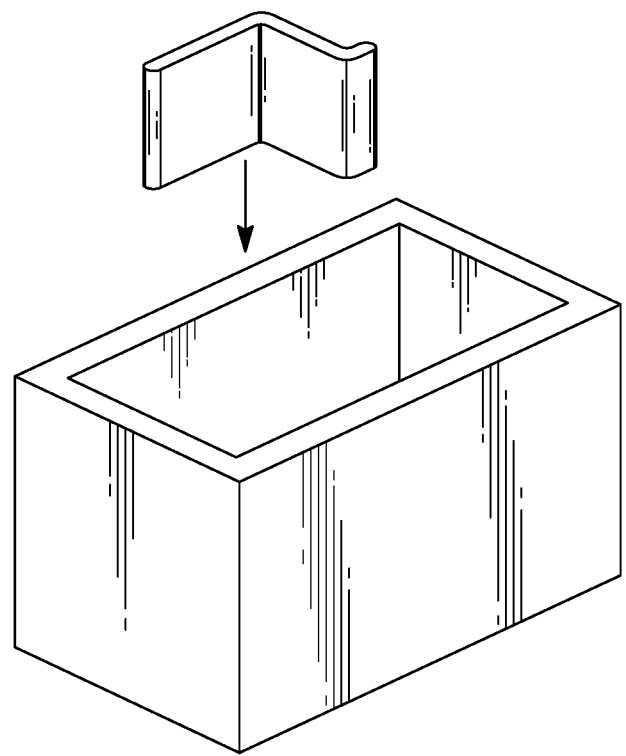
FIG. 18A show the pack being bent and before placement in a container such as a cooler.
Figure 18B:
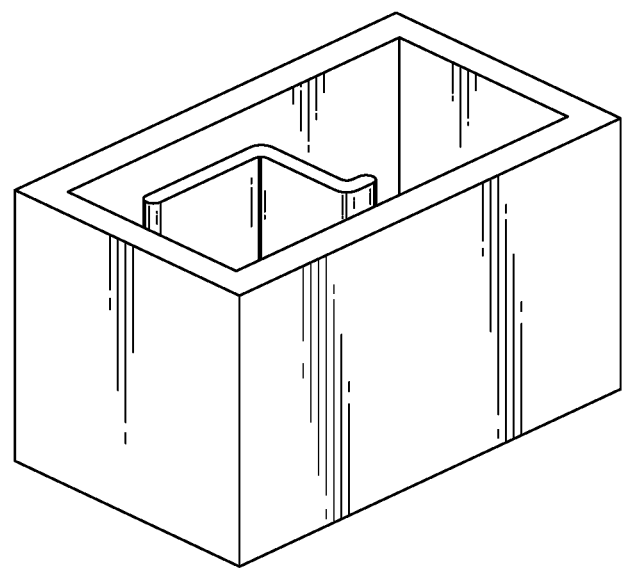
FIG. 18B shows the bent pack inside of a container.

In a further embodiment as shown in FIGS. 18A and 18B, the thermal pack 61 if a cold pouch with gel material or ice therein, may be used in food storage and allows for molding or shaping of the pack 61 to more closely fit about food items, not shown, in a container 62.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A thermal pack comprising:
a pouch containing a thermal source, the pouch having four sides defining a rectangular shape; and
a bendable and deformable support disposed within the pouch, the support being configured such that the pouch is deformed into a shape matching a contour of a body part and the pouch is maintained in the shape while applied to the body part by the support;
wherein the support comprises one or more deformable elongated members extending on three or more of the four sides of the rectangular shape, the one or more deformable elongated members each comprising two or more wires helically twisted together.

2. The thermal pack according to claim 1, wherein the pouch comprises a cavity having the thermal source disposed therein.

3. The thermal pack according to claim 1, wherein the thermal source comprises one or more of a hot source or a cold source.

4. The thermal pack according to claim 1, wherein the one or more deformable members comprise at least first, second and third deformable members disposed along at least first, second and third sides of the four sides, respectively, of an outer periphery of the pouch, the at least first, second and third deformable elongated members each comprising two or more wires helically twisted together.

5. The thermal pack according to claim 1, wherein the pouch comprises a first pouch and the thermal source is contained in a second pouch wherein the second pouch is contained in the first pouch.

6. The thermal pack according to claim 1, wherein first and second sides of the four sides each having a first length and third and fourth sides of the four sides each having a second length, the second length being longer than the first length.

7. The thermal pack according to claim 6, further comprising a first handle and a second handle connected to the thermal source at the first and second sides, respectively.

8. The thermal pack according to claim 7, further comprising a fastener for connecting the first and second handles together.

9. The thermal pack according to claim 8, wherein the fastener comprises a strap.

10. The thermal pack according to claim 1, further comprising a first plurality of connectors arranged on at least one side of the four sides of the pouch, the first plurality of connectors being configured to detachably attach to one or more of a second plurality of connecters arranged on an other pouch.

11. The thermal pack according to claim 10, wherein the first plurality of connectors are arranged on each of the four sides of the pouch.

12. A method of making a thermal pack, the method comprising:
helically twisting two or more wires together to provide at least one flexible and deformable elongated member;
providing a pouch made of a flexible material and containing a thermal source, the pouch having four sides defining a rectangular shape; and
extending the at least one flexible and deformable elongated member on three or more of the four sides of the rectangular shape, the at least one flexible and deformable member being configured such that the pouch is deformed into a shape matching a contour of a body part and the pouch is maintained in the shape while applied to the body part by the at least one flexible and deformable elongated member.

13. The method according to claim 12, further comprising connecting the pouch to an other pouch along at least one side of the pouch.

14. The method according to claim 12, wherein the extending comprises inserting the at least one flexible and deformable elongated member into a pocket formed along at least the three or more sides of the rectangular shape of the pouch.

15. A thermal pack comprising:
a pouch containing a thermal source, the pouch having four sides defining a rectangular shape;
a bendable and deformable support disposed within the pouch, the support having two or more wires helically twisted together, the support being configured such that the pouch is deformed into a shape matching a contour of a body part and the pouch is maintained in the shape while applied to the body part by the support; and a first plurality of connectors arranged on at least one side of the four sides of the rectangular shape of the pouch, the first plurality of connectors being configured to detachably attach to one or more of a second plurality of connecters arranged on an other pouch wherein the support comprises one or more deformable elongated members extending on three or more of the four sides of the rectangular shape.

16. The thermal pack according to claim 15, further comprising the other pouch having a second plurality of connecters arranged on at least one side of the other pouch, wherein the pouch and the other pouch are connected along the at least the one side of the pouch and the at least one side of the other pouch.

* * * * *